United States Patent [19]

Morse et al.

[11] Patent Number: 5,513,662
[45] Date of Patent: May 7, 1996

[54] PREPARATION OF BONE FOR TRANSPLANTATION

[75] Inventors: Brenda S. Morse, Chamblee; Clement D. Dioh, Marietta, both of Ga.

[73] Assignee: Osteotech, Inc., Eatontown, N.J.

[21] Appl. No.: 184,164

[22] Filed: Jan. 21, 1994

Related U.S. Application Data

[63] Continuation-in-part of Ser. No. 815,394, Dec. 31, 1991, Pat. No. 5,333,626.

[51] Int. Cl.⁶ .................................................. A61L 33/00
[52] U.S. Cl. ........................... 128/898; 604/28; 623/16; 422/27
[58] Field of Search .................. 623/16–18, 66; 606/76, 78; 422/28, 33, 27; 128/898, 202.12; 604/28

[56] References Cited

U.S. PATENT DOCUMENTS

| | | |
|---|---|---|
| 3,318,774 | 5/1967 | Dingwall . |
| 4,020,183 | 4/1977 | Asculai et al. . |
| 4,169,123 | 9/1979 | Moore et al. . |
| 4,315,919 | 2/1982 | Shanbrom . |
| 4,412,985 | 11/1983 | Shanbrom . |
| 4,456,589 | 6/1984 | Holman et al. . |
| 4,526,751 | 7/1985 | Gartner . |
| 4,553,974 | 11/1985 | Dewanjee . |
| 4,637,931 | 1/1987 | Schmitz . |
| 4,654,464 | 3/1987 | Mittelmeier et al. . |
| 4,678,470 | 7/1987 | Nashef et al. . |
| 4,695,536 | 9/1987 | Lindstrom . |
| 4,801,299 | 1/1989 | Brendel et al. . |
| 4,923,677 | 5/1990 | Simon et al. . |
| 4,946,792 | 8/1990 | O'Leary . |
| 4,950,296 | 8/1990 | McIntyre . |
| 4,994,030 | 2/1991 | Glowczewskie et al. . |
| 5,037,437 | 8/1991 | Matsen, III . |
| 5,053,049 | 10/1991 | Campbell . |
| 5,071,648 | 12/1991 | Rosenblatt . |
| 5,112,354 | 5/1992 | Sires . |
| 5,120,656 | 6/1992 | O'Leary et al. . |
| 5,298,254 | 3/1994 | Prewett et al. . |
| 5,336,616 | 8/1994 | Livesay et al. . |

FOREIGN PATENT DOCUMENTS

| | | |
|---|---|---|
| 952189 | 8/1982 | U.S.S.R. . |
| 964545 | 7/1964 | United Kingdom . |
| 91 01723 | 2/1991 | WIPO . |
| WO92/04031 | 3/1992 | WIPO . |

OTHER PUBLICATIONS

"Removal of Bone Marrow From the Cancellous Bone Space of Large Intercalary Bone Grafts", Gates K., Burnett A., Conley M., Hart R. and Wolfinbarger L., Jr., LifeNet Transplant Services, Virginia Beach, VA and Center for Biotechnology, Old Dominion University, Norfolk, VA.

"Use of Detergents in Bone Marrow Solubilization and Potential Toxicity Towards Recipient Cells", K. Gates, J. Lee, M. Zhang and L. Wolfinbarger, LifeNet Transplant Services, Virginia Beach, VA and Center for Biotechnology, Old Dominion University, Norfolk, VA.

A commercial advertisement of merchandise available for purchase from Advanced International Marketing, Inc., 8421 Wabash Ave., St. Louis, Missouri, 63134, Med–Clean Mark II Bone Processing Unit.

U.S. Department of Health and Human Services/Public Health Service, "Transmission of HIV Through Bone Transplantation: Case Report and Public Health Recommendations", *Morbidity and Mortality Weekly Report*, 37, 1988, pp. 597–599.

(List continued on next page.)

*Primary Examiner*—C. Fred Rosenbaum
*Assistant Examiner*—Perry E. Van Over
*Attorney, Agent, or Firm*—Elliot M. Olstein; Raymond J. Lillie

[57] ABSTRACT

A method of preparing bone for transplantation in which the internal matrix of the bone is contacted with an atmosphere at less than ambient pressure. The method may additionally, include a further step in which the bone is maintained in contact with a decontaminating agent or a detergent during the period of contact with the atmosphere.

24 Claims, 4 Drawing Sheets

OTHER PUBLICATIONS

S. J. Withrow et al., "Evaluation of the Antiretroviral Effect of Various Methods of Sterilizing/Preserving Corticocancellous Bone", *Transactions of the Orthopaedic Research Society*, 16, 1990, p. 226.

P. Gasper, "The Virucidal Capacity of a Surfactant/Iodophor–Based Viral Inactivation Process for Bone Allografts", a monograph available from Cryolife, Inc., 2211 New Market Parkway, Suite 142, Marietta, GA 30067, (404) 952–1660.

B. S. Morse, "A New Surfactant/Iodophor–Based Viral Inactivation Process (VIP™) for Preparation of Bone Allografts", presented at the 16th Annual Meeting of the American Association of Tissue Banks, San Diego,, Aug. 1992, available in printed form from Beach International, Inc., 11770 Bernardo Plaza Court, San Diego, CA 92128, or from Cryolife, Inc., 2211 New Market Parkway, Suite 142, Marietta, GA 30067, (404) 952–1660.

M. D. Farmer, "Procurement of Deep Tissues and Bones", item 10 at p. 9, Tissue Bank Coordinator Manual, available from, Navy Tissue Bank, U.S. Navy Hospital, San Diego, CA.

N. M. Shutkin, "Homologous–Serum Hepatitis Following the Use of Refrigerated Bone–Bank Bone", *The Journal of Bone and Joint Surgery*, 36–A(1), 1954, pp. 160–162.

G. W. Hyatt, et al., "Bone Grafting. The Procurement, Storage, and Clinical Use of Bone Homografts", Instructional Course Lectures, vol. XIV, Chapter VIII, The American Academy of Orthopaedic Surgeons, Ann Arbor, MI, USA, 1957.

B. E. Buck, et al., "Human Immunodeficiency Virus Cultured From Bone. Implications For Transplantation", *Clinical Orthopaedics and Related Research*, 251, 1990, pp. 249–253.

G. Furlini, et al., "Antibody Response to Human Immunodeficiency Virus after Infected Bone Marrow Transplant", *European Journal of Clinical Microbiology and Infectious Diseases*, 7, 1988, pp. 664–665.

R. Kakaiya, et al., "Tissue Transplant–Transmitted Infections", *Transfusion*, 31(3), 1991, pp. 277–284.

W. W. Tomford et al. "1983 Bone Bank Procedures", *Clinical Orthopaedics and Related Research*, 174, 1983, pp. 15–21.

W. Gump "Disinfectants and Antiseptics," in Kirk–Othmer Encylcopedia of Chemical Technology, vol. 7, Third Edition, John Wiley & Sons, New York, 1979, pp. 793–833.

W. W. Tomford, et al., "A Study of the Clinical Incidence of Infection in the Use of Banked Allograft Bone", *The Journal of Bone and Joint Surgery*, 63–A(2), 1981, pp. 244–248.

C. F. Lord, et al., "Infection in Bone Allografts, Incidence, Nature, and Treatment", *The Journal of Bone and Joint Surgery, 70–A(3), 1988, pp. 369–376.*

M. Bonfiglio, et al., "The Immune Concept: Its Relation To Bone Transplantation", *Annals of the New York Academy of Sciences*, issue of 1955, pp. 417–433.

S. H. Doppelt, et al., "Operational and Financial Aspects of a Hospital Bone Bank", *The Journal of Bone and Joint Surgery*, 63–A(9), 1981, pp. 1472–1481.

D. R. Dirschl et al., "Topical Antibiotic Irrigation in the Prophylaxis of Operative Wound Infections in Orthopedic Surgery", *Orthopedic Clinics of North America*, 22(3), 1991, pp. 419–426.

F. C. Reynolds, et al., "Clinical Evaluation of the Merthiolate Bone Bank and Homogenous Bone Grafts", *The Journal of Bone and Joint Surgery*, 33–A(4), 1951, pp. 873–883.

D. J. Prolo and S. A. Oklund, "Sterilization of Bone by Chemicals", *in Osteochondral Allografts–Biology, Banking and Clinical Applications,* G. E. Friedlaender et al., eds. Chapter 22, Little, Brown and Company, Boston, MA, 1983, pp. 233–238.

G. E. Friedlaender and M. C. Horowitz, "Immune Responses to Osteochondral Allografts: Nature and Significance", *Orthopedics*, 15(10), 1992, pp. 1171–1175.

H. J. Mankin, et al., "Current Status of Allografting for Bone Tumors", *Orthopedics*, 15(10), 1992, pp. 1147–1154.

N. L. Scarborough, "Current Procedures for Banking Allograft Human Bone", *Orthopedics*, 15(10), 1992, pp. 1161–1167.

T. I. Malinin, "Acquisition and Banking of Bone Allografts", *in Bone Grafts and Bone Substitutes*, M. B. Habal and A. H. Reddi, eds., Chapter 19, W. B. Saunders, Company, Philadelphia, PA, 1992, pp. 206–225.

PREPARATION OF BONE FOR TRANSPLANTATION

The present application is a continuation-in-part of U.S. application Ser. No. 07/815,394, itself filed Dec. 31, 1991, now U.S. Pat. No. 5,333,626 the entire description, claims and figures of which are incorporated herein, by reference, in their entirety.

FIELD OF THE INVENTION

The present invention relates to methods of processing bone for transplantation. More particularly, the invention is directed to the provision of decontaminated bone, transplant of which minimizes substantially exposure of the transplant recipient to contaminating pathogens or immunogenic material.

REPORTED DEVELOPMENTS

The procurement and processing of human bone for transplantation is a complicated task which requires the coordinated efforts of several groups including the donor's family, the hospital staff, the local procurement group, the blood specimen processing laboratory, the bone processing laboratory, the transplant patient, and the transplant team.

A prime consideration is minimization of the risk of transferring potentially harmful diseases to tissue recipients.. In fact, provision of bone tissue safe for transplantation provides a very special challenge as immunogenic material and also microorganisms and viruses can be found deep within the internal matrix of bone samples.

In this regard, blood samples may be analyzed at the processing laboratory for a variety of known infectious agents including, for example, Human immunodeficiency virus (HIV-1)

Human immunodeficiency virus (HIV-2)

Human T cell lymphotropic virus (HTLV-1)

Hepatitis B

Hepatitis C

Cytomegalic virus (CMV)

Treponema pallidum (syphilis).

With respect to the serious clinical consequences resulting from the transplanting of contaminated bone see, for example, Kakaiya et al., "Tissue transplant-transmitted infections," *Transfusion* 31 (3), 1277–284, 1991; Shutkin, "Homologous-serum hepatitis following use of refrigerated bone-bank bones, report of a case", *Journal of Bone and Joint Surgery*, 16-A(1), 160–162, 1954. Transmission of human immunodeficiency virus (HIV) via bone as well as bone marrow has also been reported. "Transmission of HIV through bone transplantation case report and public health recommendations" *Novbid. Mortal. Weekly Rep.*, 37, 597–599, 1988; Furlini et al., "Antibody response to human immunodeficiency virus after infected bone marrow transplant", *Eur. J. Clin. Microbiol. Infect. Dis.* 7(5) 554–665, 1988. HIV has been cultured from fresh as well as refrigerated bone and freeze-dried bone. Buck et al. "Human immunodeficiency virus cultured from bone. Implications for transplantation", *Clin. Ortho.*, 251, 249–253, 1990. Additionally, protection of technicians at the bone processing laboratory is of great concern because of the serious potential for transmission of HIV and hepatitis B.

A further and very important consideration with respect to the design of bone processing methodologies is avoiding or minimizing immune response (including transplant rejection) in the recipient patient to donor macromolecules remaining in the transplanted bone, such as collagens, and cell surface antigens of the major histocompatibility complex or other glycoproteins. See, for example, Friedlander and Horowitz, *Orthopedics*, 15(10), 1171–1175 (1992), and Mankin, et al., Id., at 1147–1154.

Accordingly, there is a great need for bone processing methods that decrease the risk of recipient immunological response or disease transmission associated with the use of, and preparation and procurement of, transplantable bone. In this regard it is also important to recognize that even if state of the art donor screening methodology is used, recent infections in a particular donor may not be detected, thereby underscoring the importance of improved cleaning and decontaminating treatments that offer prophylactic protection against potential, or as yet undetected, infectious agents.

The combination of donor screening and antibiotic treatments traditionally employed during bone processing reduces, but do not limit to an acceptable level, the risk of transmission of known viral contaminants and a variety of bacteria. See, for example, Scarborough, N. L., *Orthopedics*, 15(10), 1161–1167 (1992), and Malinin, T. I., "Acquisition and Banking of Bone Allografts", in *Bone Grafts and Bone Substitutes*, Habal and Reddi, eds., Chapter 19, pp. 206–225, W. B. Saunders Company, Philadelphia, Pa. (1992). As aforementioned, currently-available methods offer no prophylactic protection from viruses, select bacteria, and fungi which are common flora in humans or in a hospital environment. Although the sensitivity and specificity of screening tests for such pathogens are high, screening tests are not foolproof, and false negatives may result from, for example, low antibody levels (e.g., recent infection or immunodeficiency) or even technician error. Furthermore, screening tests may be useful only to identify known infectious agents. Additionally, the aforementioned traditionally-used antibiotic antibacterial cocktails currently in use do not readily kill all types of bacteria. For example, a commonly used polymyxin/bacitracin solution (50,000 units bacitracin/500,000 units polymyxin B) does not inactivate *Proteus* species. Furthermore, traditional antibiotic cocktails have no significant effect on viruses or fungi.

There are also significant limitations on the extent to which decontaminating agents have been used successfully to penetrate and to decontaminate matrix of bone. See Prolo and Oklund, "Sterilization of Bone by Chemicals", in *Osteochondral Allografts-Biology, Banking and Clinical Applications*, Friedlaender et al., eds., Chapter 22, pp. 233–238, Little, Brown and Company, Boston, Mass. (1983). Bone matrix contains potentially removable materials, for example, marrow, cells and lipid that impede access of decontaminating agents deep into bone matrix where, as aforementioned, infectious agents or immunogenic macromolecules may be present.

Certain of the difficulties encountered in extracting removable materials from the bone matrix are described, but not resolved, according to Great Britain Patent Specification 964,545, published in 1964.

The '545 Specification describes a procedure for using a fat solvent (for example, a chloroform/methanol mixture) for cleaning of bone. Substantial periods of time are involved that are inconsistent with preferred bone banking procedures, such as to rapidly match a donor bone piece of appropriate size for a recipient. An additional disadvantage stated to be inherent in this methodology is that it appears to be restricted to a particular series of steps that must be performed in a particular order. If this is not done, immunogenic donor proteins are stated to remain in the bone owing to in situ denaturation thereof caused by the fat solvent.

These and other difficulties associated with the provision of decontaminated bone suitable for transplantation are resolved according to the practice of the invention.

SUMMARY OF THE PRESENT INVENTION

The present invention relates to the discovery that manipulation of the atmospheric pressure to which internal matrix of bone is subjected during the cleaning and or decontamination thereof is particularly effective in the provision of bone suitable for transplantation. Accordingly, there is provided a method of preparing bone for transplantation, said bone containing internal matrix itself comprising removable material, said method comprising the step of contacting said bone with an atmosphere at less than ambient pressure. In a preferred aspect said method comprises a further step of contacting said bone or said matrix thereof with a solution comprising a decontaminating agent or a detergent.

Representative of clinical indications that may be treated with the decontaminated bone produced according to the practice of the invention are knee and hip surgery and transplants of femoral heads, proximal tibias, and distal femurs.

According to the practice of the present development it has also been determined that lipid in the matrix of bone interferes substantially with the cleaning and decontamination thereof. An important aspect of the invention therefore provides a method of treating internal matrix of bone that contains a predetermined amount of removable material, said matrix containing also a predetermined amount of lipid that immobilizes substantially said removable material, said method comprising the step of contacting said matrix with an atmosphere at less than ambient pressure for a time effective to reduce said lipid content below said predetermined amount thereof.

A further aspect to the invention provides a method of treating bone that contains internal matrix itself comprising a predetermined amount of removable material having substantial affinity for said bone, said method comprising the step of contacting said matrix with an atmosphere at less than ambient pressure, and then maintaining said atmosphere in contact therewith for a time effective to reduce said amount of removable material below said predetermined value thereof.

Additionally, the invention provides for a method wherein bone is subjected to elevated temperature before, during, or after contact with an atmosphere at less than ambient pressure.

These and other aspects, features and advantages of the present invention are described according to the Detailed Description of the invention that follows directly hereafter.

DETAILED DESCRIPTION OF THE PARENT INVENTION

Figure 1:
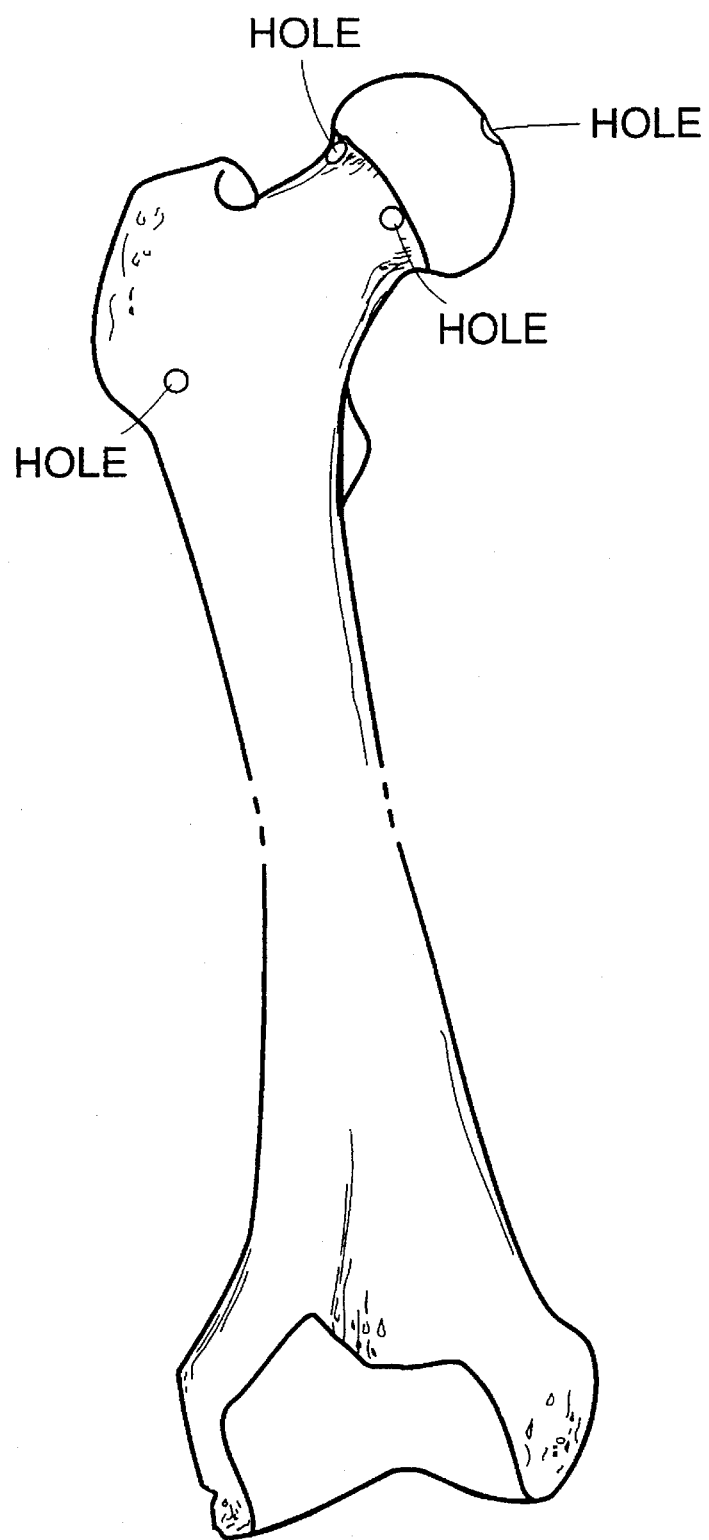
FIG. 1 is a diagram of a femur showing the site of drilled holes, suitable for facilitating access to removable material in the bone.
Figure 2A:
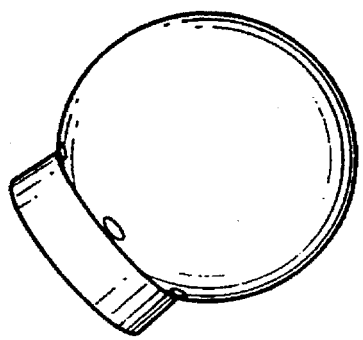
FIG. 2 is a diagram of a femoral head showing the site of drilled holes, suitable for facilitating access to removable material in the bone.
Figure 2B:
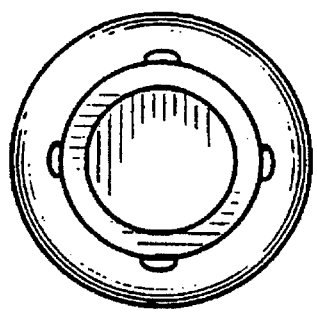

In accordance with the invention there is provided a simple, safe and effective method for treating bone and making it suitable for transplantation comprising:

a) contacting said bone with a global decontaminating agent effective to inactivate bacteria, fungi, virus and parasites;

b) cleaning said bone; and c) terminally decontaminating said cleaned bone by contacting it with a global decontaminating agent effective to inactivate bacteria, fungi, virus and parasites.

The invention also provides a method of cleaning bone which can be used in step (b) of the method described above and comprises contacting the bone with detergent under high pressure washing conditions at elevated temperatures.

For purposes of this disclosure, the term "bone" is used in the most general sense and includes all types of human or animal bone tissue, including whole bones, bone pieces, bone blocks with attached connective tissues such as ligaments and tendons, as well as ground bone preparations and ground demineralized bone preparations.

Initial or primary decontamination is accomplished by contacting the bone with a global decontaminating agent effective to inactivate bacteria, virus, fungi and parasites.

Contact time should be sufficient to effectively inactivate infectious agents. Preferably the bone is soaked in the global decontaminating solution for at least 2 or more minutes, preferably 10 or more minutes and most preferably at least one or more hours. During this primary decontaminating soaking, the bone may be removed from the solution for debridement of gross outer tissue and fat and then returned to the solution for further soaking.

The global decontaminating agent should be effective to inactivate bacteria, virus, fungi and parasites. Preferable decontaminating agents are the iodophors. Useful iodophors include polyvinyl pyrrolidone-iodine (PVP-I or povidone iodine) preparations available commercially from the Purdue-Frederick Company, ISP (formerly GAF), and BASF. PVP-I preparations useful in the practice of the invention include those of molecular weight less than 20,000 such as PVP-Iodine 17/12 of BASF.

It has been determined that preferred PVP-I preparations are those of molecular weight less than 100,000, and particularly having a median molecular weight of about 35,000 or a k value of about 26–32, for example, PVP-Iodine 30/06 of BASF.

Alternatively, suitable iodophor solutions may be prepared by mixing together a solution of the complexing agent (polyvinyl pyrrolidone in the case of PVP-I) having the desired molecular weight and molecular iodine in amounts sufficient to give the desired available iodine concentration. For example, an available iodine concentration of about 1% by weight may be obtained by dissolving 90 g of PVP in water, then with stirring adding 10 g of iodine, and finally adding sufficient water to bring the total volume to 1 liter. Other ratios of PVP to iodine may be used to obtain a PVP-I solution providing the desired available iodine concentration. Suitable available iodine concentrations are 0.03 to 1% by weight of iodine to solution, preferably 0.1% to 0.5%.

Other decontaminating agents which have been found to inactivate a wide range of infectious agents (including bacteria, fungi, parasites and virus) are hydrogen peroxide, ethanol, ozone, ethylene oxide, irradiation and use of the above in combinations, and with PVP-I.

The global decontaminating agent solution should be of a concentration effective to inactivate bacteria, virus, fungi and parasites. The iodophor concentration of a primary decontaminating solution is preferably in the range of 0.5 to 10% and most preferably 1 to 5% by weight with an available iodine concentration of 0.05 to 1%, preferably 0.1 to 0.5% by weight. PVP-I concentration is preferably in the range of 0.5 to 10% and most preferably 1 to 5% by weight of PVP-I, with an available iodine concentration of 0.05 to 1%, preferably 0.1 to 0.5% by weight.

The primary decontaminating solution may include a detergent, preferably in a concentration of 0.1 to 5% of the solution, more preferably 1 to 3%, and most preferably 0.1 to 1% by weight. Anionic, cationic, amphoteric and nonionic detergents are suitable. Preferable detergents are nonionic detergents like the polyethoxyethylene ethers (for example those marketed under the registered trademark Triton® of Rhom & Haas by Union Carbide) or the polyoxyethylene sorbitan fatty acid esters (Tween series marketed by ICI and Sigma among others). Most preferably the detergent is octylphenoxypolyethoxyethanol (Triton X-100® Rhom & Haas). Of the polyoxyethylene sorbitans, polyoxyethylene (20) sorbitan monooleate (Tween® 80) is most preferable. Advantageously, primary decontamination is effected by soaking the bone in a solution of 0.1 to 5% PVP-I and 1% (by weight) Triton X-100® for at least 2 or more minutes, preferably 10 or more minutes and most preferably at least one or more hours.

It has recently been determined that a most advantageous primary decontamination procedure involves soaking the bone in a solution of 1 to about 5% of PVP-I, without detergent, for at least about 1 to 2 hours. Preferably, owing to the ratio of free iodine to complexed iodine at the various concentrations of PVP-I, it has been determined that a most preferable modification of this step involves first soaking the bone in 5% PVP-I for about ½ to 1½ hours followed by debridement, and a further soaking in 1% PVP-I for about ½ to 1½ hours.

As Example 1 shows, the preliminary decontamination step of the invention is more effective than the prior art antibiotic cocktail. PVP-I is the preferred decontaminating agent due to its rapid action, the wide spectrum of infectious agents which it can inactivate (virus as well as bacteria, fungi and parasites) and its relatively low toxicity to human tissue. Furthermore, PVP-I has been found to inactivate HIV. The preliminary decontamination step not only protects the bone recipient by significantly reducing the risk of infection from the bone, but also protects laboratory technicians. The primary decontaminating solution, whether containing PVP-I, or PVP-I and detergent, furthermore renders the bone easier to clean by initially loosening or softening soft tissue, lipids, and blood products.

Cleaning after primary decontamination may be effected by conventional methods but is preferably effected by contacting bone with a detergent in such a way as to remove fat, marrow and other debris. The detergent lyses cells (e.g., blood cells) dissolves fat, and solubilizes proteins which comprise the bone marrow. The cleaning procedure may include agitation and/or elevated temperatures. Vigorous agitation is most preferable and can be effected by a gyratory shaker. Such washing produces bone which has negligible marrow, cells, fat and debris and thus adds an additional margin of safety for the transplant recipient by removing cells that may harbor infectious agents, and/or biomolecules that may cause an immune response.

Suitable, preferable and most preferable detergents are the same as those described above for the primary decontamination step. Detergent concentration is recommended to be about 0.1% to 5%, more preferably 1 to 3% and most preferably about 0.1 to 1%, by weight. Although iodophor can be added to the detergent containing solution in a concentration of 0.1 to 10%, it has been determined to be preferable to omit addition thereof.

Most advantageously, the bone is cleaned with a detergent solution under high pressure washing conditions at elevated temperatures. High pressure washing conditions provide a force sufficient to drive the cleaning solution into internal matrix of the bone. Such high pressure washing conditions include, for example, vigorous agitation, such as with a gyratory paint can shaker, or high pressure lavage such as with a high pressure (or velocity) liquid jet stream. Suitable paint can shakers include those manufactured by Red Devil, preferably model #0-5400-OM (615 rpm and 0.25 horsepower). The pressure of the liquid jet stream is preferably 100 to 3,000 psi and most preferably 500 to 1,500 psi. Most preferably the liquid jet stream is sterile and includes detergent. Cleaning is accelerated significantly and is more thorough if effected at temperatures within the range of 20° to 80° C., and preferably at an elevated temperature of 37° to 80° C., most preferably at about 50° to 65° C. High pressure washing effectively loosens marrow and progressively removes debris within the cancellous bone matrix. Following this high pressure washing procedure the bone is strikingly cleaner and whiter than bone processed by standard methods (See FIG. 5).

To expedite cleaning the solution may be changed, for example by transferring the bone to fresh solution, during the cleaning operation. Preferably the solution is changed at least two times. After cleaning, detergent may be finally removed by repeated washing with sterile water. A biologically acceptable alcohol such as ethanol may also be used to remove the detergent. If an alcohol is used it must be removed by rinsing with sterile water.

If bone blocks with attached connective tissue are to be cleaned, the connective tissue (tendons, ligaments, menisci, for example) should be covered with a sterile covering such as plastic wrap or sterile drape during the cleaning procedure so that contact with the detergent is avoided.

The bone may be further cleaned and decontaminated by exposing it to hydrogen peroxide, which also has bactericidal properties. After washing with detergent, the bone is transferred to a 0.5 to 10%, preferably 3%, hydrogen peroxide solution for a time sufficient to allow for additional whitening and removal of trace fat. Agitation may be applied. Incubation time is suitably 5 to 120 minutes, preferably 5 to 60 minutes, and most preferably 15 to 30 minutes. After the treatment, residual peroxide is removed by extensive washing with sterile water.

After cleaning the bone is finally decontaminated prior to packaging. This terminal decontamination is effected by contacting the bone with a global decontaminating agent for at least about 2 or more minutes, preferably at least about 10 or more minutes and most preferably 30 to 60 or more minutes. A most preferable global decontaminating agent is polyvinylpyrrolidone iodine at 1% (w/v).

When cartilage or connective tissue is present the decontaminating and cleaning solutions preferably contain sodium chloride, or another biologically acceptable salt, in an amount sufficient to prevent the PVP-I from concentrating in the cartilage or connective tissue. Preferably 0.01 to 0.75M NaCl, and most preferably 0.15M NaCl, is used.

The global decontaminating agent used for terminal decontamination may be removed from the bone by washing with sterile water, or left on as a thin coat to further protect the bone against infectious agents. The thus-coated bone may be lyophilized.

Most preferably a PVP-I coat is allowed to form. PVP-I solution adhering to the bone imparts a rich golden amber color, which can serve as an indicator that the bone has been treated. If desired, the amber bone may be lyophilized directly, packaged, and stored at room temperature, preferably in amber jars. While various methods of lyophilizing tissue are known in the art, a process that has been found suitable for lyophilizing bone is freeze-drying for about 10 to 168 hours, preferably about 20 to 28 hours. Residual PVP-I on the lyophilized bones continues to offer protection until removed by washing or by the body fluids after implantation. Likewise, the bone may be coated with other suitable global decontaminating agents, PVP-I, or mixtures thereof.

Alternatively, the residual global decontaminating agent may be removed by rinsing with sterile water or inactivated by chemical reaction. The originally off-white bone color may thus be restored. Iodophors may be chemically inactivated by adding a reducing agent such as sodium ascorbate or thiosulfate, to the soaking solution after the required soaking time has elapsed. The reducing solution should be of a molarity and amount sufficient to inactivate the remaining molecular iodine. For example, 50 to 100 microliters of 1M sodium ascorbate solution should be sufficient to inactivate 10 mls of 1% PVP-I. This treatment turns the solution back from dark brown to a clear color and returns the bone to its natural color.

After the terminal decontamination step, the bone may be lyophilized or cryopreserved or fresh frozen for storage.

It should be appreciated by those skilled in the art that bone treated in the manner herein disclosed is suitable for all therapeutic uses for which bone is required, for example bone transplants, hip surgery and knee surgery.

DETAILED DESCRIPTION OF THE PRESENT INVENTION

Introduction

There is a recognized need for technologies capable of providing bone for transplantation that minimize effectively the serious risks of infectivity and immunogenicity associated with current transplant procedures. Unfortunately, the preparation of bone for transplant purposes has proved to be a very difficult problem owing to the presence in bone of structure (the internal matrix) that is recognized to substantially prevent penetration into the bone of effective amounts of substances useful in the cleaning and decontaminating thereof.

Bone is a specialized form of connective tissue that owes its hardness to the deposition of mineral substance into a soft organic matrix. Internal matrix of bone is understood in the art to refer to the materials found within bone whether of the (compact) cortical or the (spongy) (trabecular) cancellous type that are typically found to be organized into structure therein, and including, for example, bone fluids, extravascular and vascular fluids, calcified bone matrix, bone marrow (including red or fatty marrow) and the cells thereof, osteogenic cells, extracellular and intracellular lipids, and erythrocytes. Such materials (except, generally, calcified bone matrix) are recognized in the art to be removable materials, that is, they are preferably removed from the bone upon the cleaning and/or decontamination thereof, although it is recognized also that such materials have affinity, typically a substantial affinity, for bone and the defined spaces therein that they occupy. For the purposes of the invention, removable material of the matrix is said to have substantial affinity for a bone sample when a water-based cleaning or decontaminating solution in contact therewith cannot dislodge a substantial portion of the material when said solution is provided for about 1 to 5 minutes as a stream at room temperature from a source at about standard household tap pressure.

As provided in the parent embodiment of the invention, the aforementioned materials of the internal matrix interfere substantially with the cleaning and decontamination of bone. Broadly stated, the developments of the present embodiment of the invention provide for the important discovery that removal of such matrix materials, whether directly or indirectly, from bone intended for transplantation is facilitated greatly by placing the bone sample in an environment where it is contacted with (or placed in) an atmosphere of less than ambient pressure. According to the practice of the invention, ambient pressure is understood to mean about 1.0 atmosphere of gas pressure.

It has also been discovered according to the practice of the invention that lipid whether found as extracellular or intracellular lipid in the matrix tends to substantially immobilize removable components of the matrix (for example, marrow, cells, antigenic macromolecules, or debris from any thereof, and also lipid itself) preventing or limiting removal of such components by cleaning and decontamination procedures such as, for example, those described in the parent embodiment herein. Without being limited as to theory it is believed that aqueous cleaning or decontaminating solutions cannot effectively penetrate the inner bone matrix due to the presence of packed cells of the marrow and a hydrophobic barrier of lipid.

This effect is substantial since it is well known, for example, that fat cells are an important component of bone matrix, with yellow bone marrow being composed almost entirely of fat cells (see, for example, Tanaka, Y and Goodman, V. R., "Electron Microscopy of Human Blood Cells", Chapter 7 at page 380, Harper and Row, New York, N.Y. 1972. Accordingly, a preferred aspect of the present embodiment of the invention involves treating internal matrix of bone that contains a predetermined amount of removable material, said matrix containing also a predetermined amount of lipid that immobilizes substantially said removable material, said method comprising the step of contacting said matrix with an atmosphere at less than ambient pressure for a time effective to reduce said lipid content below said predetermined amount thereof.

An amount of lipid is stated to substantially immobilize removable material of the bone matrix when a water-based cleaning or decontaminating solution cannot dislodge said material when the solution is provided in contact with the bone sample for about 1 to 5 minutes as a stream at room temperatures from a source at about standard household tap pressure.

For the purposes of the invention, "lipid" includes all substances recognized as such by the art including, for example, triglycerides, free fatty acids, cholesterol and esters thereof, and "polar" lipids such as lecithin and sphingomyelin.

Preparation of Transplantable Bone

Bone suitable for transplantation is prepared using a process that comprises the step of contacting bone with an atmosphere at less than ambient pressure and at least one further step, whether before or after said contacting, comprising also contacting the bone with a solution comprising a detergent or a decontaminating agent. Preferably, at least one such further step is performed after contact with a low pressure atmosphere in order to take advantage of the opening of channels into the matrix caused by removal of lipid. The parent embodiment of the invention defines a large number of additional cleaning or decontaminating steps, including those performed at elevated temperature, that may be combined in a sequence to define a particular cleaning or decontamination procedure. Preferred decontaminating agents include, as before, ethyl alcohol, hydrogen peroxide, chlorhexidine, hypochlorite and idophors such as PVP-I (particularly having a molecular weight of less than about 100,000). In connection herewith, elevated temperature refers to a temperature of about 37° C. or higher, preferably about 37° C. to about 80° C., and, generally, most preferably about 50° C. to about 65° C., although optimum temperatures can be determined for individual samples. Cleaning and decontaminating steps may also be performed, according to the practice of the parent and the present embodiments of invention, at below 37° C. Preferred and representative examples of the present embodiment are provided in Examples 6 through 9 below.

The term "bone", as used according to the practice of the present development of the invention is used in the most general sense and includes all types of human or animal bone tissue, including whole bones, bone pieces, bone blocks with attached connective tissues such as ligaments and tendons, the sample being capable of restoring natural bone integrity in a patient, and of bearing weight at a transplant site, such bone pieces typically having at least one dimension of approximately 10 mm or larger. Samples of bone that are representative of those useful in the practice of the invention include the following products that have been available from Cryolife Orthopaedics, Inc., Marietta, Ga. (typically, sold under the trademark VIP, Viral Inactivation Process): cancellous block; cancellous cubes; condyle, whole; cortical strips and struts; dowel, bicortical cloward; dowel, bicortical crock; dowel, ilium tricortical crock; dowel, patellar tricortical crock; femur, distal; femur head; fibula, whole; humerus head; ilium, whole; ilium plate; mandible hemi; pelvis, whole; rib, medium; rotator cuff; and ulna, whole. Excluded from the definition of bone herein are ground bone preparations, ground demineralized bone preparations and bone shavings all such excluded categories having in common the following features: (1) they are not weight bearing bone structures in that they cannot support weight in a therapeutic context, for example, being less than about 5 mm of thickness of cortical bone of a tibia or femur in a patient; and (2) owing to the very high surface to volume ratio of the shaving or ground bone sample, the lipid thereof does not participate substantially in immobilization of removable material therein.

Use of any pressure of less than ambient value thereof is within the practice of the invention although it has generally been found (see Examples 6 to 10 which follow) that pressures of about 0.7 atm or below are generally needed for useful effect, with pressures of about 0.3 atm to about 0.1 atm being generally most preferred. It is noted that large bone pieces (for example femoral head, distal femur and proximal tibia) having sizeable cancellous regions are best treated at pressures of about 0.2 to 0.13 atm. Optimum atmospheric pressures for use with particular bone pieces can be determined for particular applications and may depend on the specific sequence and combination of other cleaning or decontamination steps that have preceded the one or more low atmospheric pressure-contact steps. Optimum temperature for effecting contact of the bone with pressure below ambient is generally about 20° to 60° C. Similarly, optimum times for maintaining pressure below ambient are generally in the range of 30 to 60 minutes but can be determined for each application by monitoring progress of blood and lipid extraction (see Example 10). Generally use of gas pressure below ambient for less than two minutes will be ineffective and use for longer than five hours will confer no further benefit.

In connection with the practice of the invention, however, and with respect to optimizing the conditions of low atmospheric pressure useful therefor, it has been determined that use of too low a pressure is also generally ineffective. The use of too low a pressure causes a freezing effect not unlike that seen in lyophilization equipment, that is, the removable materials of the bone leave the bone quickly at first but then further cleaning or decontamination fails owing to freezing in situ of the materials including lipid. The precise low pressure at which such a failure occurs varies as a function of numerous parameters including the freezing temperature of the lipids, blood and marrow, and bone surface area, with 0.001 atm being representative of an unacceptable pressure. The range of unacceptably low pressures may be determined for any particular combination of bone sample(s) and equipment.

It has been discovered also that direct or indirect contact of an atmosphere at less than 1.0 atm pressure with the internal matrix of a bone sample is facilitated by the drilling of one or more holes of sufficient depth into the sample (see, for example, Examples 7 to 10 and FIGS. 1 to 4 below). In connection with this aspect of the invention the following serve as guidelines for the practice thereof:

(1) whenever possible, the hole or holes should be drilled into a region of the bone sample that bears minimal weight as would be recognized in the art. For example, see FIGS. 1 to 4 in the case of a femur.

(2) preferably the holes are between 5 and 100 mm deep depending on the nature of the bone sample with about 10 to about 30 mm depth being preferred for many human bone samples (see Examples 7 to 10), including the human femur. Preferably the holes are between about 0.5 and about 3 mm in diameter, although the number, size, depth and placement of holes is subject to the broad discretion of the practitioner.

The following representative Examples serve to illustrate and more particularly describe the parent and the present embodiments of the invention.

EXAMPLE 1

Step 1: Primary Decontamination

Human bone was harvested, cultured and found to be contaminated with a variety of bacteria and fungi including:

*Staphylococcus* species (coagulase negative)

*Enterococcus* species

*Candida albicans*

*Acinetobacter anitratus*
*Klebsiella pneumoniae.*

The ilium was soaked in a solution of 5% PVP-I (polyvinylpyrrolidone-Iodine, C15 complex from GAF). The gross outer tissue and fat was removed, the bone returned to 5% PVP-I for a total time of one (1) hour and the bone was tested (in five replicates) for residual contamination. The following table shows a comparison of the present method with incubations in saline, the positive control, and bacitracin/polymyxin cocktail.

| Solution | Total Microorganisms/bone |
| --- | --- |
| Pre-treatment | 8,700 |
| Post-treatment | |
| Saline | 11,000 |
| Antibiotic cocktail | 4,300 |
| 5% PVP-I | 330 |

Results indicate the 5% PVP-I is superior to the antibiotic treatment in reducing the number of infectious organisms.

Step 2: Cleaning

The bone was transferred to a screw top jar containing 1% (by volume) octylphenoxypolyethoxyethanol, (Triton X-100®) at 37° C. and shaken vigorously in a paint can shaker (Model No. 0-5400-OM manufactured by Red Devil) for 10 minutes. After transferring the bone to a clean solution of warm 1% Triton X-100®, the bone was incubated overnight (about 15 to 18 hours at 37°–42° C.) and shaken vigorously for 10 minutes. The bone was transferred to fresh 1% Triton X-100® and again shaken vigorously for 10 minutes. Any remaining marrow was removed by lavage with sterile water.

Next, the bone was placed in 3% hydrogen peroxide, shaken for 10 minutes, and incubated for a total time of 60 minutes.

The cleaned bone was washed thoroughly with sterile water by lavage and repeated rinses until there was no evidence of detergent foam.

Step 3: Terminal Decontamination

The cleaned bone was placed in 1% PVP-I at room temperature, shaken vigorously for 10 minutes and incubated for a total time of 30 minutes, and removed from the solution.

Step 4: Storage

If desired, the PVP-I may be allowed to dry on the bone giving the bone a rich golden color and additional protection against infective agents. The coated bone may then be lyophilized. Likewise, if desired, the bone may be coated with PVP by allowing PVP to dry on the bone.

EXAMPLE 2

Step 1. Primary Decontamination

Human knee en bloc is harvested by the local procurement agency, packaged, and shipped on wet ice to a bone processing laboratory.

At the processing laboratory, the knee is placed into 1–5% PVP-I, 0.15M sodium chloride for 10 to 60 minutes.

Step 2. Tissue Preparation and Cleaning

The following knee tissues with adjoining bone blocks are removed:
- patella tendon
- posterior cruciate ligament
- anterior cruciate ligament
- menisci The pieces are trimmed to remove excess tissue and fat. The ligament or tendon is wrapped in a sterile covering (e.g., plastic wrap or sterile drapes) while the bone blocks are cleaned by lavage with warm (40°–65° C.) 1% Triton X-100® followed by thorough rinsing with sterile water or saline.

Step 3. Terminal Sterilization

The tissues are placed in 1% PVP-I, 0.15M sodium chloride, gently shaken for 1 hour at room temperature, and rinsed thoroughly with sterile water or saline. Each piece is cryopreserved, packaged, and stored in liquid nitrogen.

EXAMPLE 2 (Supplement)

It has been determined that with respect to the use of Triton X-100® in Step 2 of Example 2, that 0.1% is a preferred concentration thereof.

EXAMPLE 3

Step 1. Primary Decontamination

Human diaphysial bones were harvested by the local procurement agency, packaged, and shipped on wet ice to a bone processing laboratory.

The processing laboratory placed the bones into 5% PVP-I, 1% Triton X-100® for 10 to 60 minutes.

Step 2. Tissue Preparation and Cleaning

The bones were debrided to remove excess tissue and fat, placed in 1% PVP-I, 1% Triton X-100®. Next, the bones were further cleaned by lavage and incubation in warm (40°–65° C.) 1% Triton X-100® followed by thorough rinsing with sterile water.

The bones were ground into chips in a bone mill, rinsed with sterile water, and lyophilized. The chips were ground to a finer size in a Tekmar mill.

Step 3. Demineralization

The bone powder was demineralized with cold 0.6N hydrochloric acid, and rinsed with sterile water.

Step 4. Terminal Sterilization

The demineralized powder was placed in 1% PVP-I for 1 hour, rinsed thoroughly with sterile water. The powder was transferred to vials, lyophilized, packaged, and stored at room temperature.

EXAMPLE 4

Terminal Sterilization with Inactivation of PVP-I

A bone, treated similarly to the bone of Example 1, was placed in 20 mls of 1% PVP-I, and incubated for 1 hour. Following incubation, 0.132 mls of 0.91 sodium ascorbate was added. The solution almost immediately became clear and after 10 minutes the bone returned to its natural off-white color.

EXAMPLE 5

This example compares results obtained by the high pressure/elevated temperature detergent cleaning method with those obtained by standard methods. After cleaning, the femoral heads were split to better show the degree the cleaning.

The femoral head shown on the right (FIG. 5) was incubated at 60° C. in 1% (by volume) Tween 80 for 2 days with periodic 10 minute agitations using a paint can shaker (Model No. 0-5400-OM manufactured by Red Devil). The femoral head was then lavaged with warm water, incubated in 3% hydrogen peroxide for 20 minutes, and then again lavaged with warm water to remove the hydrogen peroxide.

Figure 5:
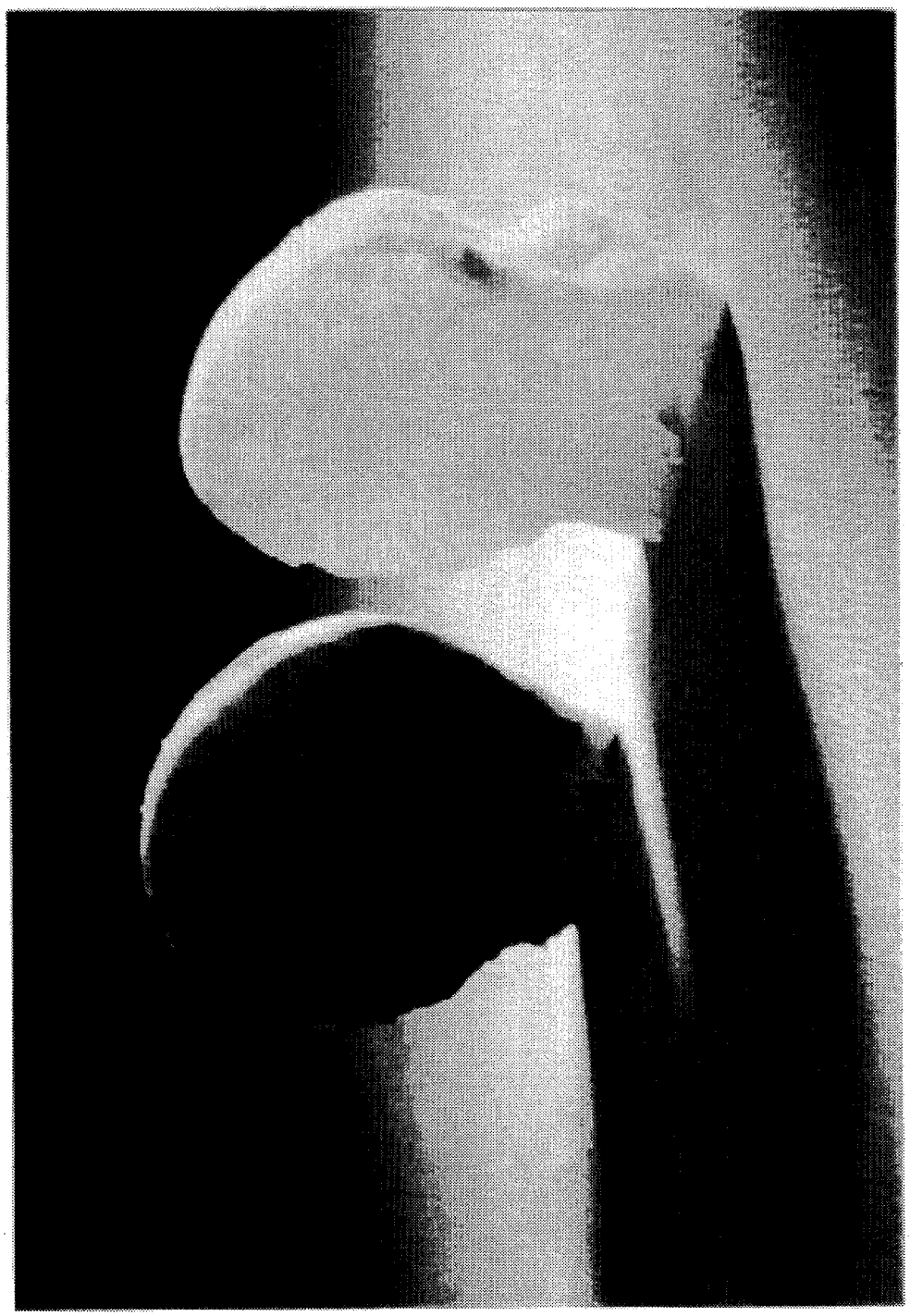
FIG. 5 is a photograph showing the improved bone produced according to the practice of the present invention.

The femoral head shown on the left was cleaned according to standard methods. It was lavaged with 60° C. water for 15 minutes; incubated in 3% hydrogen peroxide for 15–20 minutes; again lavaged with 60° C. water to remove the hydrogen peroxide; incubated in 70% ethanol for 1 hour; and again lavaged with 60° C. water to remove the ethanol. FIG. 5 is a photograph of the thus cleaned bones.

EXAMPLE 6

Treatment of a Human Femur with an Atmosphere at Less than Ambient Pressure

A femur from a human donor was debrided and cut approximately 15 cm from the distal end. The distal part was placed in a vacuum desiccator in an upright position such that the head of the femur was uppermost and the shaft was at the lowermost position. A vacuum (approximately 25 in. Hg, resulting in a chamber pressure of 0.15 atm) was applied for 1 hour using a commercial vacuum pump (Gast, model DOA-P104-AA). The temperature of the bone remained at 20° to 25° C. during the procedure. Approximately 37 ml of lipid was collected.

The bone was then washed and placed in an aqueous solution of 0.1% Triton X-100® at 60° C., and was then shaken vigorously for 10 minutes in an agitator (a commercial paint shaker, Red Devil model 5400-CM). Incubation was continued at 60° C. for about 3 hours. The bone was then rinsed with sterile water.

EXAMPLE 7

Use of an Atmosphere of Less than Ambient Pressure to Facilitate Displacement of Removable Material from Internal Matrix of Multiple Bone Samples Human bone was debrided and cut into pieces including a proximal femur, proximal tibia, cancellous dowels, and ilium wedges. The bone samples were then incubated in 5% iodophor (PVP-I, as aforementioned, BASF product 30/06) for 50 minutes, followed by transfer to, and incubation in, 1% of the above iodophor for between 30 and 60 minutes. Holes (cylindrical 1 mm×10 mm) were then drilled in the femur and tibia pieces as shown in FIGS. 1–4 (dowels excluded). All of the pieces were then placed in a vacuum desiccator such that the bone samples were positioned therein above a receiving container for the lipids. Vacuum was applied for 1 hour using the Gast model DOA-P104-AA pump resulting in a chamber pressure of 25 inches Hg (0.16 atm), with the bone being maintained at about 23° C. Approximately 37 ml of lipid and 7.5 ml of blood were collected.

EXAMPLE 8

Use of an Atmosphere of Less than Ambient Pressure to Facilitate Displacement of Removable Material from an Ilium Wedge An ilium wedge prepared according to the procedure of Example 7 (about 1.5 inches in length, 0.75 inch across side) was prewarmed for 1 hour in a solution of 0.1% Triton X-100® in water at 60° C., with occasional mild shaking, and then transferred into a 50 ml collection tube. Vacuum was applied (620 mm Hg) for 80 minutes leading to a chamber pressure of 0.15 atm, (with the temperature of the bone being maintained at 23° C.). Approximately 0.8 ml of lipid was collected over a period of 30 minutes.

EXAMPLE 9

Treatment of Human Femur Bone Samples

For this procedure, samples the right and left distal femurs of a human donor were cut at approximately 5.5 inches in from the distal ends thereof. The right side femur sample was treated by the art-recognized process described above using polymyxin/bacitracin solution whereas the left side femur sample was treated by the viral inactivation process as described directly below (see also Example 1).

Figure 4:
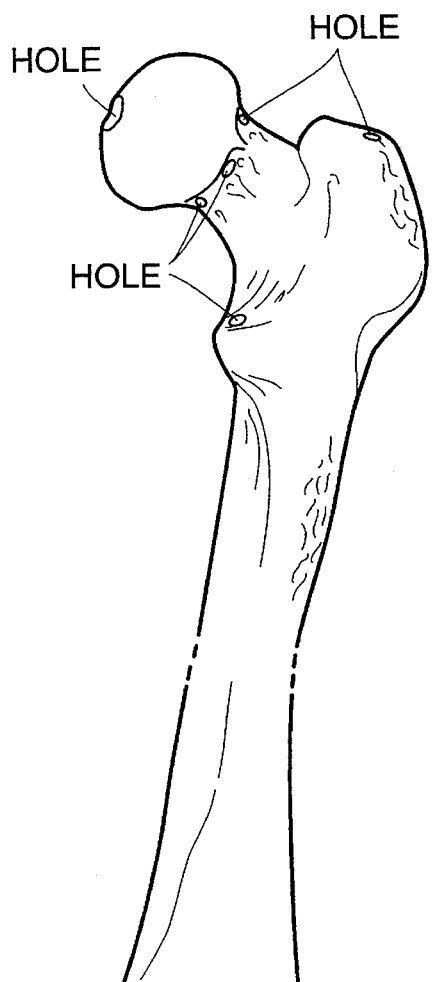
FIG. 4 is a diagram of a right femur showing the site of drilled holes, suitable for facilitating access to removable material in the bone.
Figure 3:
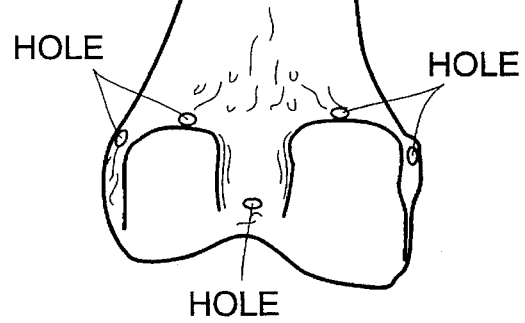
FIG. 3 is a diagram of a femoral head showing the site of drilled holes, suitable for facilitating access to removable material in the bone.

Accordingly, the left side sample of bone was soaked in 5% iodophor solution, (5% PVP-I, BASF product 30/06), for approximately 1 hour, and then transferred to a ½ liter volume of a fresh iodophor solution (1% PVP-I, BASF product 30/06) for about 1 hour, after which it was debrided. Approximately 5 holes (1–2 mm wide and 10–20 mm in depth) were then drilled through both the cortical and also the cancellous bone regions thereof as shown in FIG. 4.

After rinsing with warm water and drying, the bone was placed in a vacuum desiccator and approximately 26 mm Hg of vacuum was applied using a Gast Model DAA-V175-E8 pump for 30 minutes leading to the presence over the bone of a pressure of 0.132 atm. The temperature of the bone was approximately 23° to 35° C. or slightly warmer. Approximately 30 ml of lipid was removed by the vacuum treatment.

After warm water lavage for 5 minutes, the bone was then placed in a 0.1% surfactant solution, and agitated as in Example 8, for 10 minutes. Fresh surfactant solution was then added, and the process was repeated until the solution was fairly clear. The bone was then incubated with an additional volume of the surfactant solution for three hours at 60° C. After a rinse with water, the bone was transferred for 5–15 minutes to an aqueous solution of 3% peroxide, and then rinsed with water. The cleaned bone was then transferred to a 1% iodophor solution (PVP-I) for one hour, rinsed with water, after which the container was refilled with water. A reducing agent, sodium thiosulfate, was added to convert any residual iodine to iodide and the bone was rinsed thoroughly with water for storage.

In order to compare the transplantable bone of the invention with that made available from traditional methods, the right side femur sample was treated, as aforementioned, according to the art-recognized polymyxin/bacitracin process. Accordingly, the right side femur sample was debrided and placed in a container of warm water. The container was handshaken, the lipid-containing water discarded, and fresh hot water added. The process was repeated until the amount of lipid in the water was minimal (about 0.5 hour). Bone resulting from the traditional process retained characteristics evidencing its lesser level of clinical utility, for example, a red brown color due to residual blood and oily residue due to residual lipid.

EXAMPLE 10

Demonstration of Blood and Lipid Flow from a Femur as a Function of Atmospheric Pressure (Less than Ambient)

Effective atmospheric pressure was determined for a single piece of bone (distal human femur with holes of 1 to 2 mm drilled as shown in FIG. 4). A hand vacuum pump was used to lower the air pressure in increments of 2.5 inches Hg (about 0.08 atm each). The bone was maintained at each vacuum setting for 5 minutes and the number of blood and/or lipid drops produced was determined for each time period. Results are shown in Table 1 below.

| Vacuum (in. Hg.) | % atm | Volume (drops/5 min.) | Droplet Characterization |
|---|---|---|---|
| 0 | 1.0 | 3 | |
| 2.5 | .92 | 2 | Blood only |
| 5 | | 4 | Blood only |
| 7.5 | | 1 | Blood only |
| 10 | .66 | 5 | 2 Lipid + 3 Blood |
| 12.5 | | 8 | Lipid only |
| 15 | | 11 | Lipid only |
| 17.5 | | 18 | " |
| 20 | | 28 | " |
| 22.5 | | 38 | " |
| 25 | .16 | 82 | " |

What is claimed is:

1. A method of preparing bone for transplantation, said bone containing an internal matrix comprising removable material, said method comprising:
   (a) contacting said bone or said matrix with a solution comprising a detergent or a decontaminating agent;
   (b) contacting said bone with an atmosphere having a pressure which is less than ambient pressure; and
   (c) contacting said bone or said matrix with a solution comprising a detergent or a decontaminating agent.

2. A method according to claim 1 wherein said decontaminating agent has the capability to inactivate one or more species or strains of bacteria, fungi, virus, prions, or parasites.

3. A method according to claim 1 wherein said bone is subjected to a high pressure washing condition before or after contact with said atmosphere.

4. A method according to claim 3 wherein said high pressure washing condition comprises lavage with a stream of high velocity liquid.

5. A method according to claim 3 wherein said high pressure washing condition comprises vigorous agitation.

6. A method according to claim 1 wherein said bone is subjected to elevated temperature before, during, or after contact with said atmosphere.

7. A method according to claim 6 wherein said elevated temperature is between about 37° and about 80° C.

8. A method according to claim 7 wherein said elevated temperature is between about 50° C. and about 65° C.

9. A method according to claim 1 wherein said decontaminating agent is selected from the group consisting of ethyl alcohol, hydrogen peroxide, chlorhexidine, hypochlorite, and an iodophor.

10. A method according to claim 9 wherein said agent is an iodophor.

11. A method according to claim 10 wherein said iodophor is polyvinylpyrrolidone iodine having a molecular weight of less than about 100,000.

12. A method according to claim 1 wherein contact of said atmosphere to said matrix is facilitated by the drilling of one or more holes into said bone.

13. A method according to claim 12 wherein said one or more holes are drilled into a region of said bone that bears minimal weight.

14. A method according to claim 13 wherein said holes are between about 0.5 mm and about 3 mm in diameter.

15. A method according to claim 14 wherein said holes are between about 10 mm and about 30 mm deep.

16. A method according to claim 1 wherein said atmosphere has a pressure of about 0.7 atm or less, and is maintained in contact with said bone for between about 2 minutes and about 5 hours.

17. A method according to claim 16 wherein said atmosphere has a pressure of about 0.3 atm or less, and is maintained in contact with said bone for between about 30 and about 60 minutes.

18. A method according to claim 17 wherein said atmosphere has a pressure of about 0.2 atm or less, and is maintained in contact with said bone sample for between about 30 and about 60 minutes.

19. A method according to claim 1 that facilitates inactivation of virus.

20. Bone suitable for transplantation into a patient produced according to the method of claim 1.

21. A method of treating bone that contains internal matrix itself comprising a predetermined amount of removable material having substantial affinity for said bone, said method comprising the step of contacting said matrix with an atmosphere at less than ambient pressure, and then maintaining said atmosphere in contact therewith for a time effective to reduce said amount of removable material below said predetermined value thereof.

22. A method of treating internal matrix of bone that contains a predetermined amount of removable material, said matrix containing also a predetermined amount of lipid that immobilizes substantially said removable material, said method comprising the step of contacting said matrix with an atmosphere at less than ambient pressure for a time effective to reduce said lipid content below said predetermined amount thereof.

23. Bone suitable for transplantation into a patient produced according to the method of claim 22.

24. A method of treating bone, said bone containing a section of internal matrix having at ambient pressure and in a defined space thereof, a predetermined amount of removable material, said method comprising subjecting space external to and in contact with said matrix to an atmosphere at less than ambient pressure for a time sufficient to reduce the amount of removable material remaining in said defined space below said predetermined amount thereof.

* * * * *